(12) United States Patent
Shepherd et al.

(10) Patent No.: US 8,647,373 B1
(45) Date of Patent: Feb. 11, 2014

(54) PHOTOTHERAPY METHODS USING FLUORESCENT UV LIGHT

(76) Inventors: James G. Shepherd, Villa Hills, KY (US); John C. Dowdy, Arlington, TN (US); Robert M. Sayre, Cordova, TN (US)

(*) Notice: Subject to any disclaimer, the term of this patent is extended or adjusted under 35 U.S.C. 154(b) by 33 days.

(21) Appl. No.: 13/025,276

(22) Filed: Feb. 11, 2011

Related U.S. Application Data

(60) Provisional application No. 61/303,489, filed on Feb. 11, 2010.

(51) Int. Cl.
*A61N 5/06* (2006.01)

(52) U.S. Cl.
USPC .......................................................... 607/88

(58) Field of Classification Search
CPC .......................................................... A61N 5/06
USPC .......................................................... 607/88
See application file for complete search history.

(56) References Cited

U.S. PATENT DOCUMENTS

| | | | | |
|---|---|---|---|---|
| 3,670,193 A | * | 6/1972 | Thorington et al. | 313/487 |
| 4,177,384 A | * | 12/1979 | Wolff | 250/494.1 |
| 4,230,701 A | * | 10/1980 | Holick et al. | 514/167 |
| 4,335,120 A | * | 6/1982 | Holick et al. | 514/167 |
| 4,370,595 A | * | 1/1983 | Willemsen et al. | 313/486 |
| 4,683,379 A | * | 7/1987 | Wolff | 250/493.1 |
| 4,859,903 A | * | 8/1989 | Minematu et al. | 313/487 |
| 4,891,550 A | * | 1/1990 | Northrop et al. | 313/487 |
| 4,967,090 A | * | 10/1990 | Schlitt | 250/504 R |
| 5,503,904 A | * | 4/1996 | Yoshinaga et al. | 428/195.1 |
| 5,565,685 A | * | 10/1996 | Czako et al. | 250/504 R |
| 5,763,891 A | * | 6/1998 | Yoshinaga et al. | 250/459.1 |
| 5,892,619 A | * | 4/1999 | Chubb et al. | 359/361 |
| 6,017,360 A | * | 1/2000 | Chubb et al. | 607/88 |
| 6,129,438 A | * | 10/2000 | Chubb et al. | 362/2 |
| 6,153,879 A | * | 11/2000 | Yoshinaga et al. | 250/271 |
| 6,254,254 B1 | * | 7/2001 | Chubb et al. | 362/293 |
| 6,436,127 B1 | * | 8/2002 | Anderson et al. | 607/89 |
| 6,632,002 B1 | * | 10/2003 | Chubb et al. | 362/228 |

(Continued)

FOREIGN PATENT DOCUMENTS

| | | | | |
|---|---|---|---|---|
| JP | 63216263 A | * | 9/1988 | H01J 61/42 |
| WO | WO 2005104162 A2 | * | 11/2005 | |
| WO | WO 2006113577 A2 | * | 10/2006 | A61N 5/06 |

OTHER PUBLICATIONS

SOLARC Systems Inc., Standard Information Package, 2007. (Comments: Date printed on document. Obtained from wayback.archive.org on a Aug. 6, 2007 http://www.solarcsystems.com/pdfs/home_uvb_phototherapy_package_usa.pdf).*

(Continued)

*Primary Examiner* — Bill Thomson
*Assistant Examiner* — Manolis Pahakis
(74) *Attorney, Agent, or Firm* — Wood, Herron & Evans, LLP

(57) ABSTRACT

Vitamin D is supplemented in a human body by exposure of skin to light from a fluorescent lamp at a sub-erythemal dose of UV radiation. Wave lengths, emitted light intensities and repeat treatments without lamp refractory time are disclosed.

11 Claims, 2 Drawing Sheets

(56) References Cited

U.S. PATENT DOCUMENTS

| | | | | |
|---|---|---|---|---|
| 6,828,576 | B2* | 12/2004 | Spivak | 250/504 R |
| 6,851,814 | B2* | 2/2005 | Chubb et al. | 362/1 |
| 6,964,931 | B2* | 11/2005 | Carlyle et al. | 442/340 |
| 6,984,228 | B2* | 1/2006 | Anderson et al. | 606/9 |
| 6,984,931 | B2* | 1/2006 | Dutta et al. | 313/487 |
| 7,122,952 | B2* | 10/2006 | Dutta et al. | 313/487 |
| 7,214,464 | B2* | 5/2007 | Roberts et al. | 430/139 |
| 7,221,084 | B2* | 5/2007 | Fan et al. | 313/486 |
| 7,229,467 | B2* | 6/2007 | Spivak | 607/88 |
| 7,238,302 | B2* | 7/2007 | Fan et al. | 252/301.4 P |
| 7,288,215 | B2* | 10/2007 | Fan et al. | 252/301.4 R |
| 7,297,155 | B2* | 11/2007 | Rosenberg et al. | 607/94 |
| 7,388,219 | B2* | 6/2008 | Sauska et al. | 250/504 R |
| 7,396,490 | B2* | 7/2008 | Marking et al. | 252/301.4 P |
| 7,419,621 | B2* | 9/2008 | Marking et al. | 252/301.4 R |
| 7,449,129 | B2* | 11/2008 | Marking et al. | 252/301.4 R |
| 7,497,974 | B2* | 3/2009 | Fan et al. | 252/301.4 P |
| 7,667,407 | B2* | 2/2010 | Schlitt et al. | 313/635 |
| 7,846,352 | B2* | 12/2010 | Marking et al. | 252/301.4 R |
| 7,921,853 | B2* | 4/2011 | Fiset | 128/898 |
| 8,173,230 | B2* | 5/2012 | Justel et al. | 428/34.4 |
| 2005/0010249 | A1* | 1/2005 | Minamoto et al. | 607/2 |
| 2006/0085053 | A1* | 4/2006 | Anderson et al. | 607/94 |
| 2006/0220519 | A1* | 10/2006 | Fan et al. | 313/486 |
| 2007/0069624 | A1* | 3/2007 | Dutta et al. | 313/486 |
| 2007/0221883 | A1* | 9/2007 | Marking et al. | 252/301.4 R |
| 2007/0235689 | A1* | 10/2007 | Marking et al. | 252/301.4 P |
| 2007/0255266 | A1* | 11/2007 | Cumbie et al. | 606/9 |
| 2008/0030120 | A1* | 2/2008 | Fan et al. | 313/484 |
| 2008/0039907 | A1* | 2/2008 | Fiset | 607/94 |
| 2008/0146674 | A1* | 6/2008 | Rosenberg et al. | 514/641 |
| 2008/0213152 | A1* | 9/2008 | Marking et al. | 423/263 |
| 2008/0224592 | A1* | 9/2008 | Reich et al. | 313/487 |
| 2011/0002918 | A1* | 1/2011 | Levatter | 424/133.1 |
| 2011/0212410 | A1* | 9/2011 | Fiset | 433/29 |
| 2011/0227501 | A1* | 9/2011 | Awamoto et al. | 315/287 |

OTHER PUBLICATIONS

SOLARC Systems Inc., Lamps for Vitamind D Phototherapy, Aug. 27, 2008 (Source: http://www.solarsystems.com/lamps-forvitamin-d.html, Aug. 27, 2008, obtained from wayback.archive.org).*

Grant W. and Holick M., Benefits and requirements of Vitamin D for optimal health: a review, Alternative Medicine Review, vol. 10, 2, 2005.*

SOLARC Systems Inc., Lamps for vitamin D phototherapy, Aug. 27, 2008, Note: retrieved with the Wayback Machine with the link: www.solarcsystems.com/lamps-for-vitamin-d.html.*

SOLARC Systems Inc., Standard Information Package, Rev. 4, 2007, Note: Date on the bottom of all internal pages.*

SOLARC Systems Inc., UVB Phototherapy Equipment for Vitamin D Deficiency, Feb. 8, 2009, Note: retrieved with the Wayback Machine with the link: www.vitamin-d-phototherapy.com.*

Collins English Dictionary, definition of "foregoing".*

Shepherd et al., Reintroduction of a classic vitamin D ultraviolet source, Journal of Steroid Biochemistry & Molecular Biology 103 (2007) 686-688.*

Koninklijke Philips Electronics N.V., Effective light therapy Philips lamps for therapeutic purposes, 2007.*

Ley et al., Photoreactivation of Ultraviolet Radiation-induced Skin and Eye Tumors of *Monodelphis domestica*, Cancer Res 1991;51:6539-6542.*

Chandra et al., Treatment of vitamin D deficiency with UV light in patients with malabsorption syndromes: a case series, Photodermatol Photoimmunol Photomed 2007; 23: 179-185.*

Nagy et al., Ultraviolet Emitting Phosphor, Journal of the Electrochemical Society, Jan. 1950.*

Internatl Standard ISO 17166 CIE S 007/E "Erythema reference action spectrum and standard erythema dose" First Edition Dec. 15, 1999.

Bouillon et al., "Action Spectrum for the Production of Previtamin D3 in Human Skin," The International Commission on Illumination, vol. 174, pp. 1-12, (2006).

* cited by examiner

PHOTOTHERAPY METHODS USING FLUORESCENT UV LIGHT

PRIORITY CLAIM

Applicant claims the benefit of the filing date, Feb. 11, 2010, of U.S. provisional patent application Ser. No. 61/303,489, of the same title, which prior application is incorporated herein by reference as if wholly expressed in writing herein.

BACKGROUND OF THE INVENTION

This invention relates to the production of Vitamin D in the human body and more particularly to an improved light source and associated process to that end.

The human body's need for Vitamin D is well-known. There are traditional sources of Vitamin D for human use. For example, these include medicaments or chemical supplements, orally administered and otherwise, sunlight exposure causing Vitamin D production in human bodies and exposure to artificially created light to produce Vitamin D. These sources may be variably effective, with the efficiency sometimes resulting from the nature of the subject human being. For example, chemical sources or supplements are sometimes not processed efficiently in older bodies.

When sunlight is considered as a Vitamin D source over time, efficiency of Vitamin D production is a function of the location of exposure. Below the $37^{th}$ parallel of the earth, sufficient sunlight exposure causing Vitamin D creation in a human body is only available about five or six months per year. Above the $37^{th}$ parallel, sufficient exposure to sunlight for creation of Vitamin D in a human body only extends about five or so weeks per year.

Creation of Vitamin D in human bodies from exposure to artificial light has been known for some time, but is not without inherent drawbacks. For example, exposure to certain incandescent bulbs producing ultraviolet light (UV) in the spectral range of 250-400 nanometers (nm) has been known to cause the human body to internally produce Vitamin D since at least from about 1941. One informational source concerning UV light used in therapeutic applications is that of U.S. Pat. No. 6,828,576. Another is that of U.S. Pat. Nos. 7,297,155 and 7,229,467 and a disclosure of a lamp structure for tanning is published in the United States under Publication No. US 2007/0069624 A1 published Mar. 29, 2007. Both these patents as well as the Publication are herewith incorporated by reference as if fully expressed and set out herein.

Currently, incandescent bulbs creating UV in this spectral range consist of medium pressure mercury (Hg) vapor lamps. Such sources of ultraviolet light labeled for application to produce Vitamin D in the human body are available only from the assignee of this application and marketed under the trademark "SPERTI SUNLAMP". Such lamps require ambient heat through an electric arc to activate mercury (Hg) molecules and to form an arc for producing ultraviolet energy. Once such a lamp is activated, a cool down period of about 8-10 minutes after stoppage is required before the lamp can be restarted. Moreover, the lamp radiation is limited in the area covered. So when such lamp is used to radiate human skin from a position in close proximity to a body, the area of coverage is very small. This requires excessive overall time in front of the lamp for more universal coverage (such as by relative movement between the lamp and body), and increases the possibility of tanning, which may be an undesirable product of such light treatment used for Vitamin D production or synthesis in the human body. Said in another way, the desire to increase exposure to light for Vitamin D production is offset by the disadvantage of simultaneously increased UV exposure and tanning.

One such current incandescent bulb has a power peak at a spectral range of 366 nm which is above the optimum wave length range for Vitamin D production.

There are yet further factors which are even more detailed, significant and important to consider in the matter of exposure to human skin to light of particular wave lengths.

It is known that exposure to light in the wavelength range of about 290 nanometers ("nm") to about 320 nm can produce Vitamin D in humans. Nevertheless, exposure of human skin to light in the wavelengths of about 320 nm and higher can cause basal cell carcinoma ("bcc") and squamous cell carcinoma ("scc").

Both "bcc" and "scc" can be cured with high success rates if early detected and treated. About ten percent 10% (100,000) of skin cancer incidents in the United States (about 1,000,000 total cases), however, are of the melanoma variety. Of these, about 5% to about 10% (5000-8700) result in fatalities (these numbers and percentages of cancer incidents are exemplary approximations).

In the face of the dangers of light-caused skin cancers, the United States government and the United States medical industry have continually warned the populace against exposure to UVA and UVB containing sunlight. Sunscreens, shade, cover, clothing, reduced exposure time and the like are promoted as reducing risk. These expedients can help reduce the incidence of cancer in humans. On the other hand, reduced light exposure has the undesirable side effect of reducing natural Vitamin D supplemental production as a result of sunlight exposure of the human skin. Accordingly, taken to the extreme, the populace is warned about exposure to sunlight, but strict adherence to exposure prevention is resulting in Vitamin D deficiencies.

The adverse results of Vitamin D deficiency, such as rickets and other maladies are now more currently widespread in the United States. Nevertheless, the lack of Vitamin D supplementation by sunlight or artificial ultraviolet light has not generated significant medical attention until recently. The medical community has now begun to recognize maladies caused by Vitamin D deficiencies, some of which arise from increased attention to the warnings of the cancer-related dangers of sunlight exposure, and adherence to increasing standards of exposure limitations and prevention techniques.

Accordingly, even while the applicant is able to make and sell its various prior light products labeled to provide Vitamin D supplementation (as a function of its grandfathered status of such activities from the early 1940s), it is now desired to provide a light apparatus and a method for producing Vitamin D supplementation while significantly reducing the adverse effects of exposure to light in the cancer-causing dosage range of prior light-producing apparatus, and at the same time avoiding the cool-down periods required by incandescent sources and reducing the overall exposure times required for effective Vitamin D supplementation.

It is thus desired to enhance Vitamin D supplementation in humans by exposure to light while, at the same time, diminishing incidence of cancer in humans using light for Vitamin D supplement production.

It is also desired to produce these results together with overcoming the physical and functional disadvantages noted above respecting prior light sources.

SUMMARY OF THE INVENTION

To these ends, the invention contemplates a fluorescent light source producing a light output concentrated in the preferred range of about 290 nm to about 320 nm for Vitamin D supplementation, while reducing cancer risks and exposure to light in the wavelength ranges longer than those effective for Vitamin D production. This concentrated wavelength output, has the capacity, if not to reduce the likelihood of UVA-caused cancer, to reduce its incidents by about 90%. Moreover, the invention contemplates a heretofore unknown fluorescent source of such light, cooler running and without the refractory time required between cycles of prior incandescent light sources. The invention thus advantageously improves light production of supplemental Vitamin D in humans but contemplates hardware or source improvements as well.

Vitamin D supplementation by light initiation is thus produced, while decreasing incidence of cancer causing or accommodating light in the range of above about 320 nm.

More particularly, according to the invention, an improved fluorescent light source produces light in the wavelength range of 290 nm to 320 nm and preferably in a narrower range of about 295 nm to about 312 nm. Exposure of human skin to this light initiates a synthesizing process for production of Vitamin D in the human skin but reduces incidence of UVA-caused skin cancer from exposures to other light wavelengths.

Accordingly, it is desired to provide a light source capable of producing sufficient UV light to cause the human body, when exposed thereto, to efficiently produce or to synthesize Vitamin D, but without the drawbacks or inherent disadvantages of the current mercury vapor or other incandescent light sources noted above.

To these ends, a new and unique light source comprises a fluorescent bulb generating UV light in the approximate spectral range of about 290 nm to about 320 nm, and more particularly in the range of about 295 nm to about 312 nm.

When in use by exposure of the human body to such a fluorescent light, this unique fluorescent light source has numerous advantages over the prior incandescent mercury vapor light source which the FDA approves for labeling only by the present assignee for use to produce Vitamin D in humans. In particular, such new light source:

a) Is cooler to operate;
b) Is capable of immediate re-start, so more treatments can be accomplished in less time;
c) Produces a large area of coverage as compared with the prior mercury vapor incandescent bulb;
d) Is effective with shorter exposure times, reducing cancer risk;
e) Can be effectively used at greater distances from the body (and thus at wider coverages) than the prior mercury vapor bulbs;
f) Is less expensive than the prior mercury vapor bulbs;
g) Is more effective for use in elderly humans;
h) Uses less, if any, mercury than the prior mercury vapor bulbs; and
i) Produces less heat than the prior mercury vapor bulb.

DETAILED DESCRIPTION OF PREFERRED EMBODIMENT

According to the invention, a preferred treatment process includes exposing a portion of skin of a human body to UV light in the approximate spectral range of about 290 nm to about 320 nm emanating from a fluorescent light source, and thereby creating Vitamin D in said human body.

Figure 2:
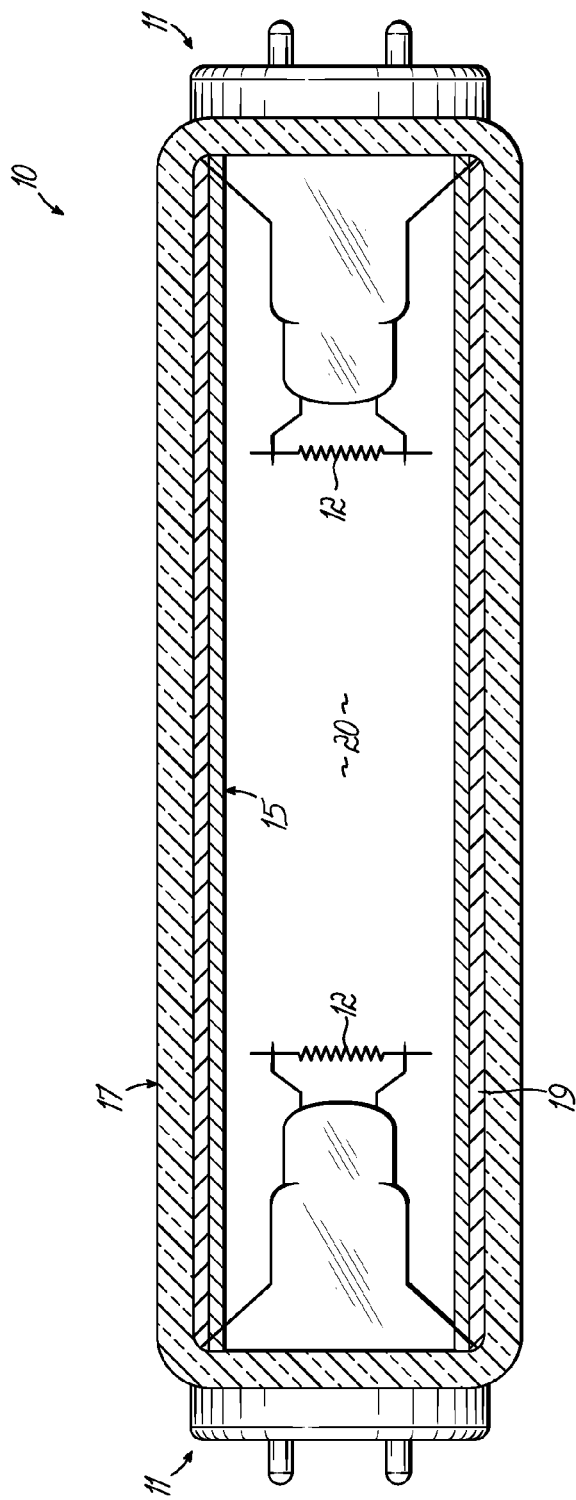
FIG. 2 is an illustrative cross-section view of a fluorescent lamp according to the invention.

One form of the fluorescent lamp itself is shown in FIG. 2 and is made by Light Sources, Inc. of 37 Robinson Boulevard, Orange, Conn. 06477 and sold to applicant under Model No. D/UV. Such a lamp, according to the invention, has the following features and characteristics.

OVERALL LENGTH: Overall lamp length, according to the invention, is from about 200 mm up to about 2400 mm. A preferred lamp dimension from base face to base face is from about 358.7 mm to about 361.2 mm. A dimension of a base face to an end of an opposite connector pin is about 365.8 mm to about 368.3 mm.

BASE: Any suitable base can be used, one suitable form being a T12 mini bipin (G-13 type). Also, a T12 RDC type base, or any other suitable custom base type could be used.

GLASS: typical fluorescent glass type available through a variety of suppliers. Glass types providing exposure properties of the lamp described herein can be used. The preferred fluorescent lamp of the invention is a T12 mode of approximately 1.5" diameter. Other diameters can be used, such as T5, T8 and T10 (15 mm, 20 mm and 32 mm). The glass envelope can be produced with a variety of transmission properties to either increase or decrease the amount of energy in UVA, UVB on ranges. Preferably, the lamp components are selected to produce a spectral power distribution peaking at about 312 nm and as shown in the FIG. 1 chart.

FILAMENTS: A typical filament mount structure is used, allowing the lamp to operate at approximately 700-800 mA. Options can be used to operate from 150 mA up to about 2000 mA.

REFLECTOR COATING: The preferred lamp of the invention is provided with an internal reflector coating to direct the light better in the direction of the user of the fixture. The reflector angle is typically 180 degrees to about 240 degrees. It can be non-existent or up to as large as 300+ degrees. Typical materials which can be used for the reflector coatings are aluminum oxide, magnesium oxide and titanium oxide. The current preferred lamp is provided with a 180 degree reflector.

GAS FILL: The interior of the lamp of the invention is filled preferably with argon gas to a pressure of about 2.2 torr. Any suitable pressure from about 1.0 torr up to about 4.0 torr can be used. Other suitable gasses can be neon, krypton, xenon and blended combinations of these depending on electrical requirements of the lamp.

MERCURY: Only a small quantity of mercury, typical of fluorescent lamps, is used. The mercury content is preferably anywhere from about 1.0 mg to about 50 mg, but is typically about 10 mg. Mercury is used to generate energy in the lamp at primarily 254 nm to excite the phosphor coating in the lamp.

PHOSPHORS: The invention contemplates use of a variety of phosphors capable of generating UVB. There are perhaps ten to twelve possible phosphor materials which can generate UVB for this application. The currently preferable phosphor material is Nichia NP 807-32 type phosphor. Also tested were NP 803 and NP 806 phosphors. Certain phosphor combinations disclosed in United States Publication No. US 2007/0069624A1, dated Mar. 29, 2007 and incorporated herein by reference, might also be used.

The phosphor and glass are chosen to provide the spectral power distribution (SPD) combinations described herein and needed for proper exposure time for the lamp and fixture combination in order to produce the desired Vitamin D production in an exposed human subject.

Figure 1:
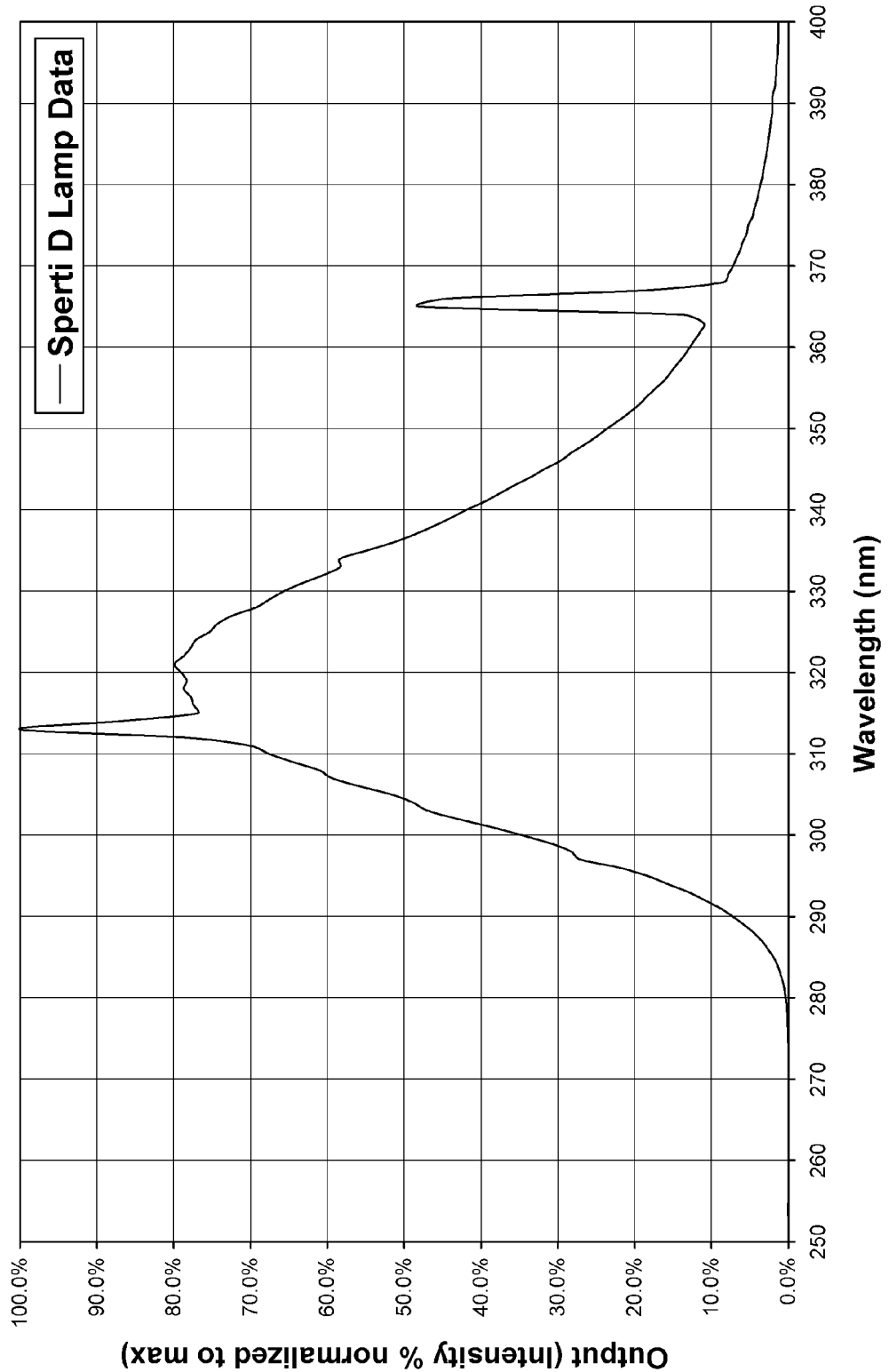
FIG. 1 is a chart illustrating the spectral power distribution (SPD) of a fluorescent lamp of the invention showing its entire performance, including the inventive range.

According to the invention, a fluorescent lamp having the foregoing parameters can be made like that of the lamp in the incorporated Publication No. US 2007/0069624 A1, published Mar. 29, 2007 but having an SPD like that of FIG. 1 herein.

Such a fluorescent lamp 10 is illustrated in FIG. 2, including end bases 11, filaments 12, phosphor coating or layer 15, a UV transmissive glass envelope 17 and reflecting layer or coating 19, all as described above. The interior 20 is filled with a gas as noted above.

The lamp of the invention has a spectral power distribution like that of FIG. 1 produced by the glass, reflective coating, phosphors and filaments. Preferably the SPD peaks at about 312 nm, is concentrated within the range of 290 nm to 320 nm (FIG. 1) and preferably 295 nm to 312 nm, such that the preferred concentrated range occurs from about 20% to about 100% and then back down to about 75-80% of the output, until precipitously declining, thus advantageously producing Vitamin D supplementation while significantly eliminating output in the shorter wavelength cancer risk range and concentrating output in the most effective Vitamin D producing range of 290 nm to 320 nm.

Another aspect of the invention and its use to produce Vitamin D supplementation in humans relates to the dosage using such source in the preferred wave length range as applied to human skin.

The dosage of light exposure on human skin is a function of intensity and time. At some point, the delivery of a given light energy over a given amount of time will typically cause a "redness" or erythermal condition in human skin.

Applicant recognizes there exists, as background, an International Technical Community Standard of ultraviolet exposure to human skin. This standard determines the upper limit of typical intensity in watts, over time, before sunburn effective energy is applied, in an attempt to state a weighting function.

Further describing such background of related photochemistry and the various standards acceptable worldwide, attention is directed to the following two documents, which applicant herewith incorporates by reference as background as if fully expressed in writing herein, in their entirety. These are:

a) A copyrighted document entitled Erythema Reference Action Spectrum and Standard Erythema Dose published on or about Dec. 15, 1999 by the "International Organization for Standardization" (known as the "ISO") and referring to the International Standard ISO 17166, prepared as Standard CIE S 007/E by the International Commission on Illumination (known as "CIE") (see ISO 17166:1999(e)) available from the CIE Central Bureau Kegelgasse 27, A-1030 Vienna, Austria (www.cie.co.at/cie/home.html); and b) A copyrighted document entitled Action Spectrum for the Production of PreVitamin $D_3$ in Human Skin published on or about 2006 by the CIE (see CIE 174:2006), available as the document cited above.

Both documents are referred to herein for background information only, not critical to description, understanding or interpretation of the invention or claims appended hereto.

The first of these above documents refers to details of the production of Vitamin $D_3$ (Vitamin D) in humans contributed to by ultraviolet radiation and discusses the photochemistry of Vitamin $D_3$ formation.

The second of these documents noted above describes the characteristics of an objective measurement of exposure described as the "Standard Erythema Dose" or "SED".

These documents suggest various spectral parameters for impingement of light on human skin to initiate cutaneously produced Vitamin D and thus provide background information related to this invention. However, there is no suggestion in these documents of the invention herein, nor of producing Vitamin D in humans through exposure to light from a fluorescent light source in the limited wavelength ranges disclosed, nor at the dosages described herein.

Accordingly, this ISO "standard erythemal dosage" or "SED" is based on the application of 100 Joules per square meter for erythemal effect over a given time. The International Commission on Illumination, or "CIE", prefers that one SED or unit is not delivered to exposed skin any faster than one minute. Accordingly, in typical tanning operations, many tanning devices produce about 4.5 SED units over a time period of about 10-20 minutes.

Given these standards against burning, the invention contemplates a weighing function or effectiveness of a light source in producing Vitamin D supplementation in humans but without violation of these noted standards.

Thus, according to the invention the fluorescent light source described above, with its concomitant advantages and light range production, is preferably used and powered in a way to produce or deliver one SED in a preferred time range of greater than one minute to an upper exposure time of about 15 to about 20 minutes or less. In this way, Vitamin D supplementation is enhanced while the deleterious effects or ineffective exposures, as noted above, are minimized.

A further discussion of the spectral power distribution (SPD) of FIG. 1 will facilitate understanding of the invention.

In FIG. 1, the SPD is of a fluorescent lamp according to the invention having only a small mercury component in the lamp. Nevertheless, the presence of such mercury results in an irregular SPD across the preferred wavelength range and elsewhere in FIG. 1. For example, the necessary component of the lamp according to the invention causes a slight "bump" or leveling of wavelength at 318, 321 and 365 nm, for example. This is quite normal for any lamp having such a mercury component.

Nevertheless, it will be appreciated the maximum power ranges of the fluorescent lamp of the invention are concentrated at wavelengths from about 290 nm to about 320 nm and more particularly from about 295 nm (20% output) to about 312 nm (about 100% output). The power of the lamp of the invention is concentrated in the Vitamin D production range, so that exposure to the lamp of this invention is most effective for Vitamin D production in the wavelengths of 290-320, while other wavelength components are reduced or diminished as to be substantially less significant.

In other words, application of light to human skin via the lamp of the invention is concentrated for the recommended dosage times in the preferred wavelength range and exposure to any undesired wavelength light is so limited that the light of the invention is effective to produce Vitamin D synthesis in humans while, at the same time, not exposing the skin in any significant way to light in other, and particularly higher, wavelengths.

What is claimed is:

1. A method of providing Vitamin D supplementation in a human body by light application while minimizing erythema, the method including:
exposing skin of a first human being to light energy emitted from a fluorescent light source in a spectral range of 295 nm to 312 nm, wherein light emitted from the fluorescent light source has an output intensity approximately at 20% at 295 nm and a peak output intensity of 100% at 312 nm, wherein the output intensity is based relative to the 100% peak output intensity at 312 nm;

and wherein the fluorescent light source is powered to deliver one Standard Erythema Dose (SED) in a time period from greater than one minute up to 20 minutes.

2. The method of providing Vitamin D supplementation of claim 1, wherein said fluorescent light source comprises: a base; and
a fluorescent lamp comprising a filament; a UV transmissive glass envelope comprising an internal reflector coating configured to provide a reflector angle between a range from 180 degrees to approximately at 240 degrees, the internal reflector coating comprising aluminum oxide, magnesium oxide, or titanium oxide; and
a phosphor material coating, which produces UVB radiation at an output intensity approximately at 20% at 295 nm and a peak output intensity of 100% at 312 nm,
wherein the output intensity is based relative to the peak 100% output intensity at 312 nm,
a gas fill comprising a gas selected from the group consisting of argon, neon, krypton, xenon, and blended combinations thereof, wherein said gas fill is present in an amount to provide an internal pressure to the fluorescent lamp between a range from approximately at 1.0 Torr to approximately at 4.0 Torr; and
mercury in an amount in a range from approximately at 1.0 mg to approximately at 50 mg, wherein the method further comprises:
operating said fluorescent light source at a current in a range from 150 mA to approximately at 2000 mA.

3. The method of claim 2, wherein operating the fluorescent light source further comprises having argon as the gas fill present in an amount to provide an internal pressure to the fluorescent lamp approximately at 2.2 Torr.

4. The method of claim 2, wherein operating the fluorescent light source further comprises having mercury present in an amount approximately at 10 mg.

5. The method of claim 2, wherein operating the fluorescent light source further comprises having argon as the gas fill present in an amount to provide an internal pressure to the fluorescent lamp approximately at 2.2 Torr, and having mercury present in an amount approximately at 10 mg.

6. The method of claim 1, wherein the phosphor material coating comprises Nichia NP 807-32 phosphor.

7. A method of supplementing Vitamin D in a human body by exposing the body to light while minimizing exposure of the body to wavelengths of light longer than 320 nm which would otherwise increase the risk of developing cancer, wherein said method includes:
exposing the body to light emitted from a fluorescent lamp comprising a filament; a UV transmissive glass envelope comprising
an internal reflector coating configured to provide a reflector angle between a range from 180 degrees to approximately at 240 degrees, the internal reflector coating comprising aluminum oxide, magnesium oxide, or titanium oxide; and
a phosphor material coating, which produces UVB radiation at an output intensity approximately at 20% at 295 nm and a peak output intensity of 100% at 312 nm,
wherein the output intensity is based relative to the 100% peak output intensity at 312 nm,
a gas fill comprising a gas selected from the group consisting of argon, neon, krypton, xenon, and blended combinations thereof, wherein said gas fill is present in an amount to provide an internal pressure to the fluorescent between a range from approximately at 1.0 Torr to approximately at 4.0 Torr; and
mercury in an amount in a range from approximately at 1.0 mg to approximately at 50 mg; and
operating said fluorescent light source at a current in a range from 150 mA to approximately at 2000 mA, wherein light emitted from the fluorescent light source has an output intensity approximately at 20% at 295 nm and a peak output intensity of 100% at 312 nm, wherein the output intensity is based relative to the 100% peak output intensity at 312 nm, and wherein the fluorescent light source is powered to deliver one Standard Erythema Dose (SED) in a time period from greater than one minute up to 20 minutes.

8. The method of claim 7, wherein operating the fluorescent light source further comprises having argon as the gas fill present in an amount to provide an internal pressure to the fluorescent lamp approximately at 2.2 Torr.

9. The method of claim 7, wherein operating the fluorescent light source further comprises having mercury present in an amount approximately at 10 mg.

10. The method of claim 7, wherein operating the fluorescent light source further comprises having argon as the gas fill present in an amount to provide an internal pressure to the fluorescent lamp approximately at 2.2 Torr, and having mercury present in an amount approximately at 10 mg.

11. The method of claim 7, wherein the phosphor material coating comprises Nichia NP 807-32 phosphor.

* * * * *

UNITED STATES PATENT AND TRADEMARK OFFICE
CERTIFICATE OF CORRECTION

| | |
|---|---|
| PATENT NO. | : 8,647,373 B1 |
| APPLICATION NO. | : 13/025276 |
| DATED | : February 11, 2014 |
| INVENTOR(S) | : James G. Shepherd et al. |

It is certified that error appears in the above-identified patent and that said Letters Patent is hereby corrected as shown below:

In the Claims:

Column 8, lines 17-28, Claim 7,     should read     -- to the fluorescent lamp
"to the fluorescent between a range"                                    between a range --

Signed and Sealed this
Eighth Day of July, 2014

Michelle K. Lee
*Deputy Director of the United States Patent and Trademark Office*